United States Patent [19]
Baugues et al.

[11] Patent Number: 5,389,082
[45] Date of Patent: Feb. 14, 1995

[54] INTRAVENOUS LINE SEPARATOR SYSTEM

[76] Inventors: Mary C. Baugues, 419 N. Maple St., Covington, Tenn. 38019; Mary C. Upchurch, 49 Hastings Way, Covington, Tenn. 38019

[21] Appl. No.: 209,710

[22] Filed: Mar. 14, 1994

[51] Int. Cl.⁶ ............................................. A61M 25/02
[52] U.S. Cl. ..................... 604/174; 24/543; 128/DIG. 36; 248/68.1; 604/180
[58] Field of Search ............... 604/174, 179, 180, 189, 604/543; 24/543; 248/68.1; 128/DIG. 26

[56] References Cited

U.S. PATENT DOCUMENTS

| D. 234,204 | 1/1975 | Miller et al. | 24/543 |
|---|---|---|---|
| 2,366,041 | 12/1949 | Morehowe | 248/68.1 |
| 3,906,592 | 9/1975 | Sakasegawa | 248/68.1 |
| 4,256,132 | 3/1981 | Gunter | 604/189 |
| 4,581,013 | 4/1986 | Allen | 604/189 |
| 4,754,534 | 7/1988 | Helwick | 24/543 |
| 4,887,335 | 10/1989 | Folkmor | 24/543 |
| 4,890,900 | 2/1990 | Baggett | 24/543 |
| 4,957,251 | 9/1990 | Hubbard | 248/68.1 |
| 4,988,338 | 1/1991 | Taylor et al. | 604/180 |
| 5,060,810 | 10/1991 | Jones | 248/68.1 |
| 5,224,679 | 7/1993 | Simons | 248/68.1 |
| 5,226,892 | 7/1993 | Boswell | 604/174 |
| 5,280,913 | 5/1993 | Clark | 24/543 |

Primary Examiner—Paul J. Hirsch

[57] ABSTRACT

An intravenous line separator system comprising a cover plate having an upper surface, a lower surface, a first end, and a second end, a plurality of U-shaped grooves formed within the cover plate, a hinge pin positioned within the first end of the cover plate, a C-shaped locking element integral with the second end of the cover plate; and a base plate having an upper surface, a lower surface, a first end, and a second end, a plurality of U-shaped grooves, the U-shaped grooves of the base plate corresponding in number and position to the U-shaped grooves of the cover plate, a hinge pin receiving means positioned at the first end of the base plate, the hinge pin of the cover plate adapted to be received within the hinge pin receiving means, the hinge pin and the hinge pin receiving means together serving to pivotally interconnect the base plate and the cover plate, a tongue locking element integral with the second end of the base plate, the C-shaped locking element adapted to receive the tongue locking element and secure the cover plate to the base plate.

2 Claims, 3 Drawing Sheets

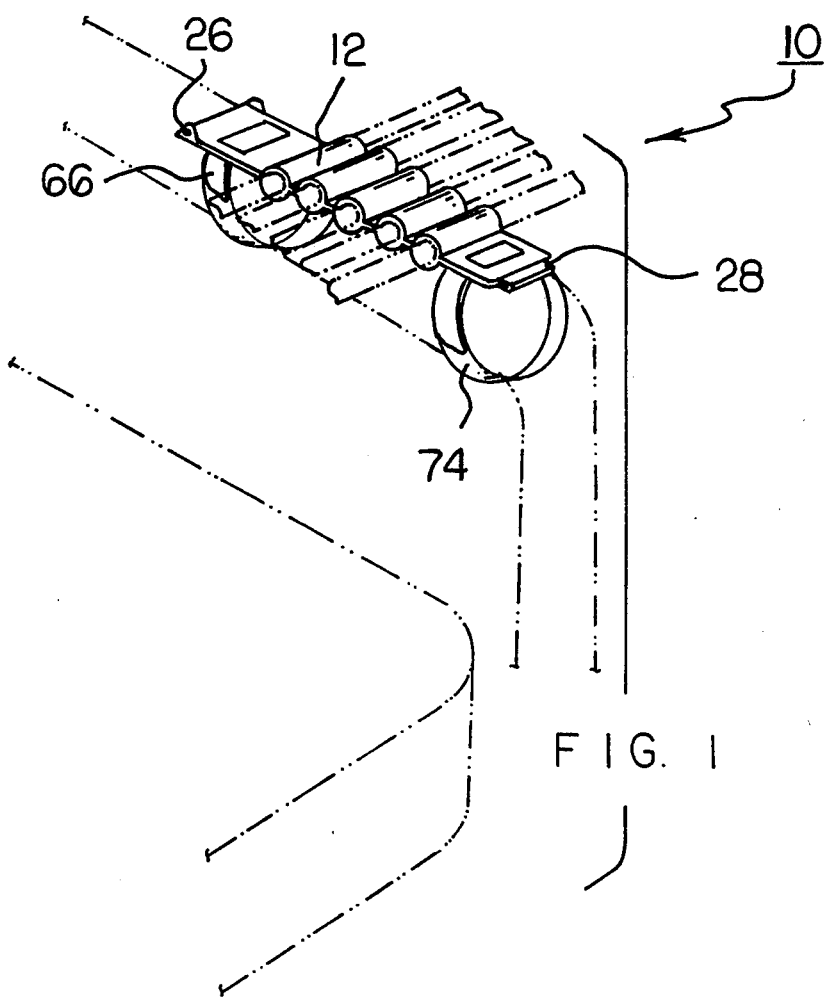
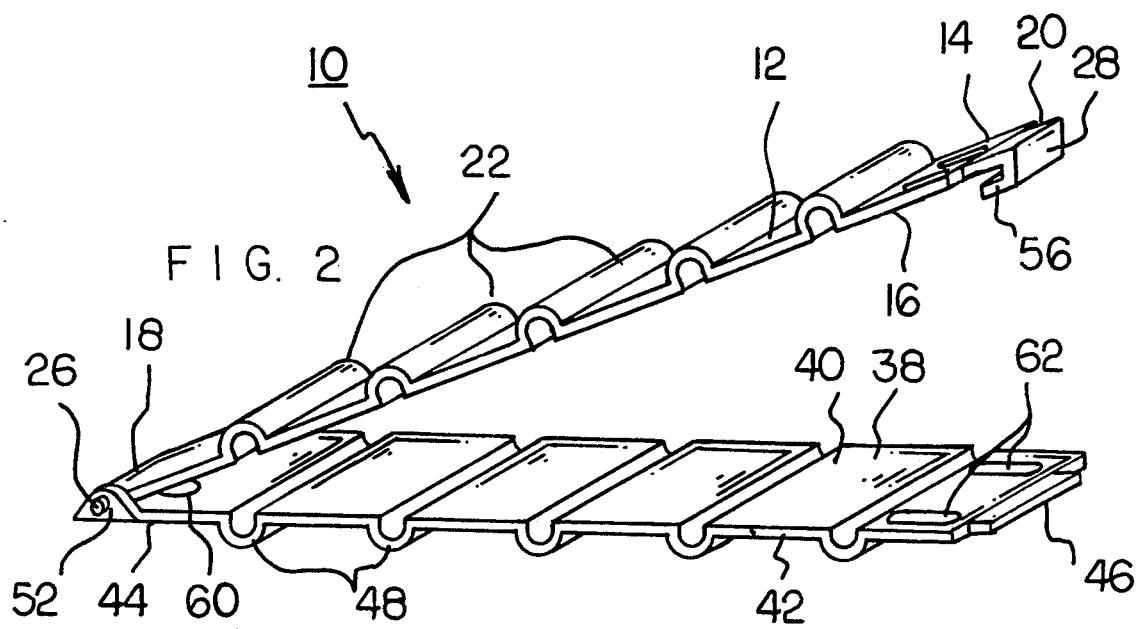

INTRAVENOUS LINE SEPARATOR SYSTEM

BACKGROUND OF THE INVENTION

1. Field of the Invention

The present invention relates to intravenous line separator systems and, more particularly, to separating a plurality of intravenous lines between sources of fluid and a patient.

2. Description of the Prior Art

The use of tubing clamps is known in the prior art. More specifically, tubing clamps heretofore devised and utilized for the purpose of holding intravenous lines are known to consist basically of familiar, expected and obvious structural configurations, notwithstanding the myriad of designs encompassed by the crowded prior art which have been developed for the fulfillment of countless objectives and requirements.

By way of example, U.S. Patent Number 3,893,468 to McPhee discloses a clamp for flexible tube and method of regulating flow in such tube.

U.S. Pat. No. 4,378,617 to Burns discloses a clasp.

U.S. Pat. No. 3,461,876 to Miller discloses a tubing clamp.

U.S. Pat. No. 4,589,171 to McGill discloses a device for holding and positioning tubing of I.V. administration set.

U.S. Pat. No. 5,115,542 to Gehres discloses a hose separator clip.

While these devices fulfill their respective, particular objectives and requirements, the aforementioned patents do not disclose an intravenous line separator system.

In these respects, the intravenous line separator system according to the present invention substantially departs from the conventional concepts and designs of the prior art, and in so doing provides an apparatus primarily developed for the purpose of separating a plurality of intravenous lines between sources of fluid and a patient.

Therefore, it can be appreciated that there exists a continuing need for new intravenous line separator which can be used for separating a plurality of intravenous lines between sources of fluid and a patient. In this regard, the present invention substantially fulfills this need.

SUMMARY OF THE INVENTION

In view of the foregoing disadvantages inherent in the known types of tubing clamps now present in the prior art, the present invention provides a new intravenous line separator system construction wherein the same can be utilized for separating a plurality of intravenous lines between sources of fluid and a patient. As such, the general purpose of the present invention, which will be described subsequently in greater detail, is to provide a new intravenous line separator system apparatus and method which has many of the advantages of the tubing clamps mentioned heretofore and many novel features that result in an intravenous line separator system which is not anticipated, rendered obvious, suggested, or even implied by any of the prior art tubing clamps, either alone or in any combination thereof.

To attain this, the present invention generally comprises a new and improved intravenous line separator system comprising, in combination, a cover plate having an upper surface, a lower surface, a first end, and a second end, a plurality of U-shaped grooves formed within the cover plate, a hinge pin positioned within the first end of the cover plate, a C-shaped locking element integral with the second end of the cover plate, a first set of oblong openings positioned within the first end of the cover plate adjacent to the hinge pin, a second set of oblong openings positioned within the second end of the cover plate adjacent to the C-shaped locking element; a base plate having an upper surface, a lower surface, a first end, and a second end, a plurality of U-shaped grooves, the U-shaped grooves of the base plate corresponding in number and position to the U-shaped grooves of the cover plate, a hinge pin receiving means positioned at the first end of the base plate, the hinge pin of the cover plate adapted to be received within the hinge pin receiving means, the hinge pin and the hinge pin receiving means together serving to pivotally interconnect the base plate and the cover plate, a tongue locking element integral with the second end of the base plate, the C-shaped locking element adapted to receive the tongue locking element and secure the cover plate to the base plate, a first set of oblong openings positioned within the first end of the base plate adjacent to the hinge pin receiving means, a second set of oblong openings positioned within the second end of the base plate adjacent to the tongue locking element, the first and second set of oblong openings of the cover plate adapted to register with the first and second set of oblong openings of the base plate; a first strap having a first end and a second end, with the ends thereof provided with a pile type fastener, the first strap adapted to be received within the second set of oblong openings of the cover plate and within the second set of oblong openings of the base plate; and a second strap having a first end and a second end, with the ends thereof provided with a pile type fastener, the second strap adapted to be received within the first set of oblong openings of the cover plate and within the first set of oblong openings of the base plate.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new intravenous line separator system apparatus and method which has many of the advantages of the mentioned heretofore and many novel features that result in an intravenous line separator system which is not anticipated, rendered obvious, suggested, or even implied by any of the prior art tubing clamps, either alone or in any combination thereof.

It is another object of the present invention to provide a new intravenous line separator system which may be easily and efficiently manufactured and marketed.

It is a further object of the present invention to provide a new intravenous line separator system which is of a durable and reliable construction.

An even further object of the present invention is to provide a new intravenous line separator system which is susceptible of a low cost of manufacture with regard to both materials and labor, and which accordingly is then susceptible of low prices of sale to the consuming public, thereby making such intravenous line separator systems economically available to the buying public.

Still yet another object of the present invention is to provide a new intravenous line separator system which provides in the apparatuses and methods of the prior art some of the advantages thereof, while simultaneously overcoming some of the disadvantages normally associated therewith.

Still another object of the present invention is to provide a new intravenous line separator system.

Yet another object of the present invention is to provide a new intravenous line separator system.

Even still another object of the present invention is to provide a new intravenous line separator system comprising a cover plate having an upper surface, a lower surface, a first end, and a second end, a plurality of U-shaped grooves formed within the cover plate, a hinge pin positioned within the first end of the cover plate, a C-shaped locking element integral with the second end of the cover plate; and a base plate having an upper surface, a lower surface, a first end, and a second end, a plurality of U-shaped grooves, the U-shaped grooves of the base plate corresponding in number and position to the U-shaped grooves of the cover plate, a hinge pin receiving means positioned at the first end of the base plate, the hinge pin of the cover plate adapted to be received within the hinge pin receiving means, the hinge pin and the hinge pin receiving means together serving to pivotally interconnect the base plate and the cover plate, a tongue locking element integral with the second end of the base plate, the C-shaped locking element adapted to receive the tongue locking element and secure the cover plate to the base plate.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the preferred embodiment of the intravenous line separator system constructed in accordance with the principles of the present invention.

FIG. 2 is a perspective view of the intravenous line separator system shown in FIG. 1 but in an opened orientation.

The same reference numerals refer to the same parts throughout the various Figures.

DESCRIPTION OF THE PREFERRED EMBODIMENT

Figure 3:
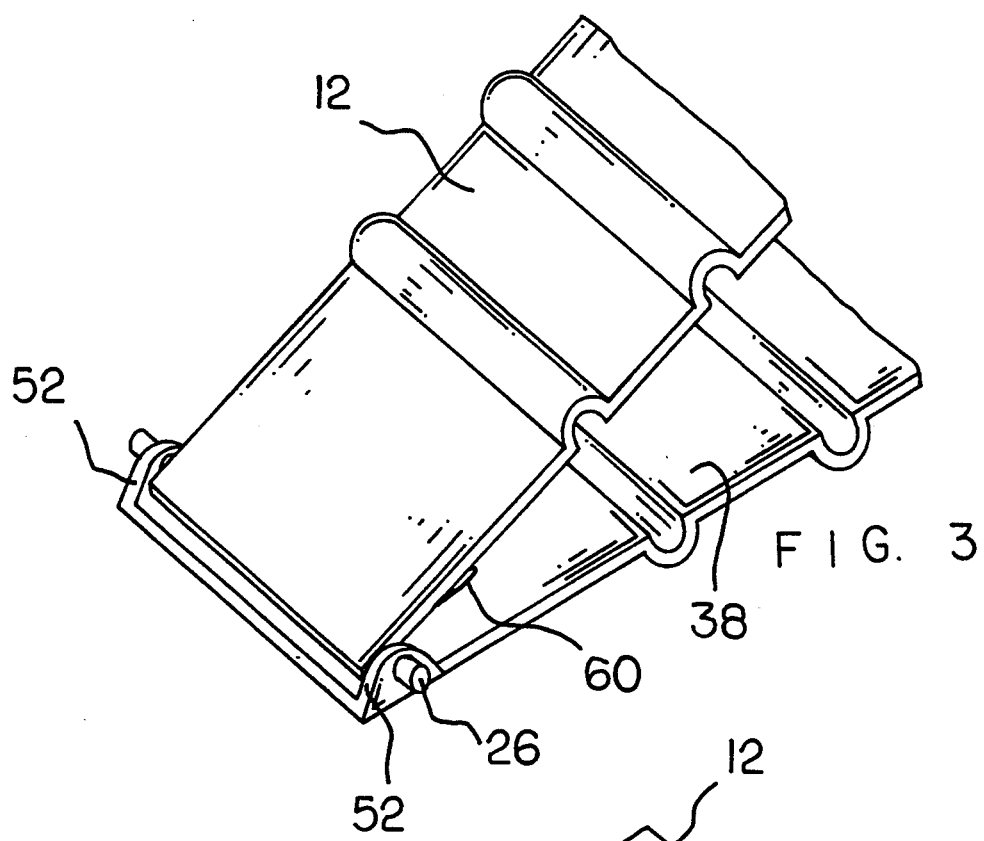
FIG. 3 is an enlarged perspective view of the first end of the intravenous line separator system of the present invention.
Figure 4:
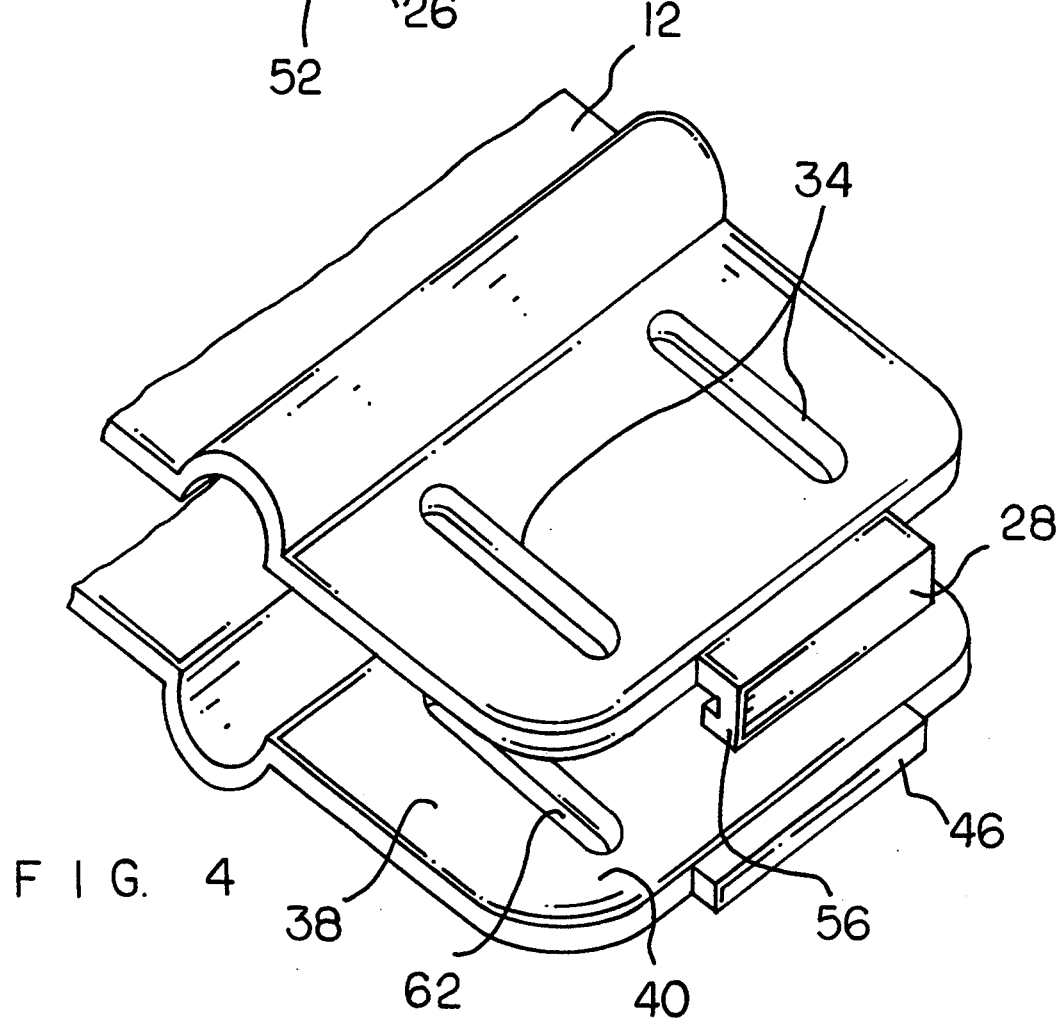
FIG. 4 is an enlarged perspective view of the second end of the intravenous line separator system of the present invention.

With reference now to the drawings, and in particular to FIG. 1 through 6 thereof, a new intravenous line separator system embodying the principles and concepts of the present invention and generally designated by the reference numeral 10 will be described.

Specifically, it will be noted that the intravenous line separator system 10 comprises, in its broadest context, a plurality of components including a cover plate, a base plate, and straps attachable with respect to the plates and the patient. The individual components are specifically configured and correlated one with respect to the other in order to attain the desired objective.

More specifically, the system 10 includes a cover plate 12. The cover has an upper surface 14 and a lower surface 16. The cover plate also has a first end 18 and a second end 20. Positioned between the two ends are a plurality of U-shaped grooves 22. The U-shaped grooves are formed at evenly spaced locations along the cover plate and are of a similar configuration.

Operable in association with the cover plate is a hinge pin 26. The hinge pin is positioned within the first end of the cover plate. In addition, a C-shaped locking element 28 is formed integral with the second end of the cover plate.

Formed within the cover plate is a first set of oblong openings 32 formed within the first end of the cover plate adjacent to the hinge pin. Also included is a second set of oblong openings 34 similar in shape to the first set of openings. Such second set of oblong openings are positioned within the second end of the cover plate adjacent to the C-shaped locking element.

Operable in cooperation with the cover plate 12 is a base plate 38. The base plate has an upper surface 40 and a lower surface 42. It also has a first end 44 and a second end 46. Formed within the base plate are a plurality of U-shaped grooves 48. The U-shaped grooves of the base plate correspond in size, number and position to the U-shaped grooves of the cover plate and, when the cover plate and base plate are coupled, form an essentially circular groove comprised of the facing U-shaped grooves of the two plates.

Also positioned on the base plate are hinge pin receiving means 52 formed as small upturned plates with apertures positioned at the first end of the base plate. The hinge pin of the cover plate is adapted to be received at its ends within the hinge pin receiving means. The hinge pin and hinge pin receiving means better serve to pivotally interconnect the base plate and the cover plate.

Securement of the two plates in operative position with respect to each other as shown in FIG. 1 is effected through a tongue locking element 56. Such locking element is formed integral with the second end of the base plate. Such locking element is C-shaped and is adapted to receive the tongue locking element and secure the cover plate to the base plate during operation and use.

In addition, a first set of oblong openings 60 is positioned within the first end of the base plate adjacent to the hinge pin receiving means. In cooperative relationship therewith, the second set of oblong openings 62 is positioned within the second end of the base plate adjacent to the tongue locking element. The first and second set of oblong openings of the cover plate are adapted to register with the first and second set of oblong openings of the base plate.

In association with the openings, there is provided a first strap 66. Such first strap has a first end and a second end. The ends thereof are provided with cooperative pile type fasteners. The first strap is adapted to be received within the second set of oblong openings of the cover plate and within the second set of the oblong openings of the base plate. When so positioned, the strap may be positioned around the area of the patient in an area for securement of the lines in operative positions.

In association with the first strap, it is preferably to use a second strap 74. The second strap, like the first strap, has a first end and a second end. The ends thereof are provided with a pile type fastener. The second strap is adapted to be received within the first set of oblong openings of the cover plate and within the first set of oblong openings of the base plate. The use of the two straps provides for maximum securement of the device and I.V. in proper position. A single strap could be used in certain applications.

Figure 5:
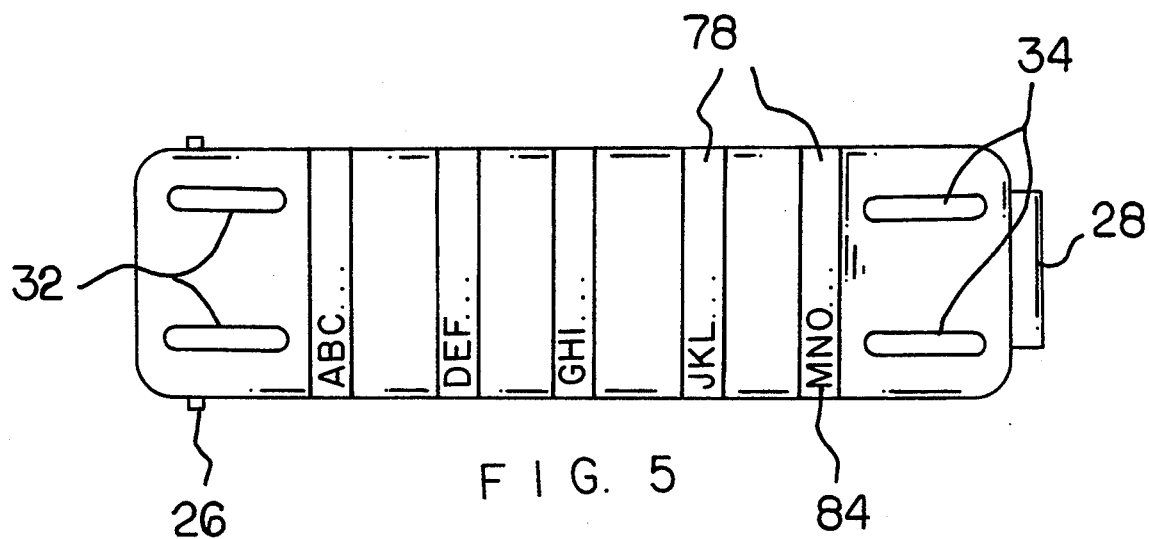
FIG. 5 is a plan view of the intravenous line separator system in accordance with an alternate embodiment of the present invention.
Figure 6:
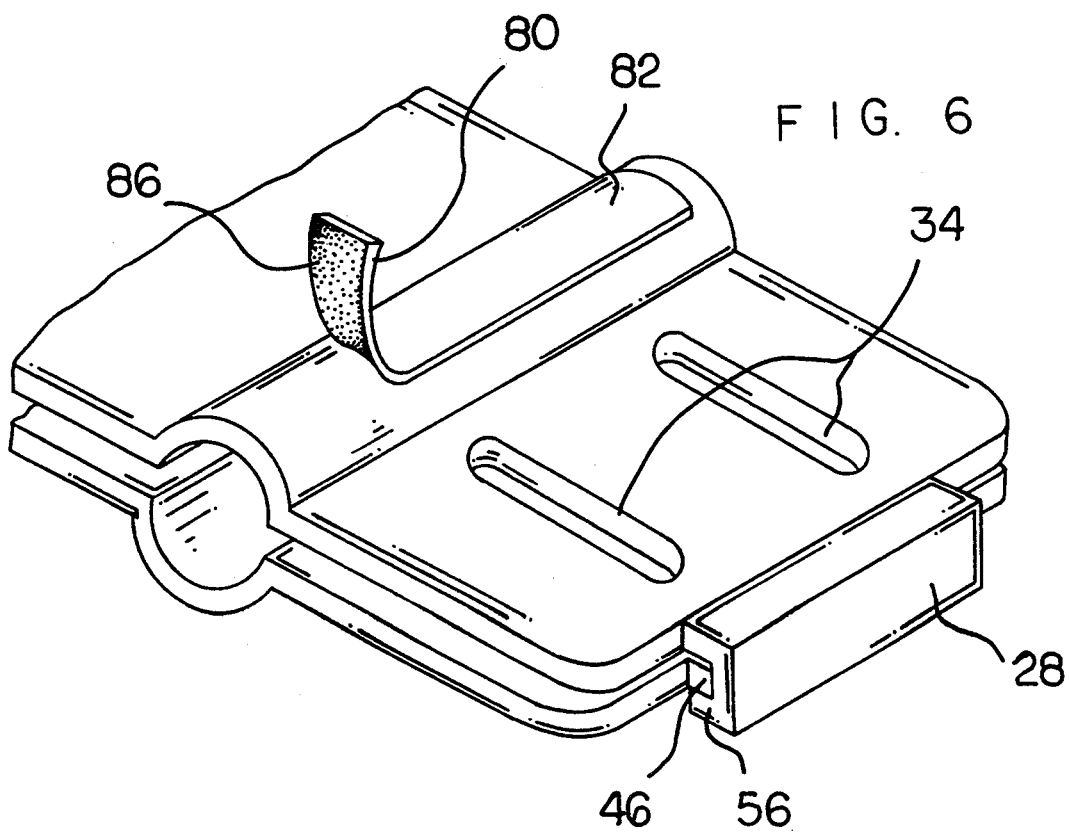
FIG. 6 is a perspective view of the second end of the intravenous line separator system shown in FIG. 5.

FIGS. 5 and 6 show an alternate embodiment of the invention. In such embodiment, the device 10 is provided with a plurality of adhesive backed labels 78. Each label includes a flexible sheet 80 with an exterior surface 82 for writing upon and an interior surface 84 having adhesive 86 for securement to the exterior of the specific U-shaped member of the cover plate. The plurality of adhesive backed labels is adapted to be secured to the upper surface of the cover plate along the U-shaped grooves. A separate label is provided for each groove. It is preferred that the plurality of adhesive backed labels receive specific writing or indicia representing of the I.V. line secured therein. In addition, the individual adhesives may be color coded for particular functions.

The present invention, as the name suggests, is designed to organize and separate the lines used for the intravenous feeding of a patient when multiple lines are in use. It is made of two elongated, rectangular plastic strips which are joined at one end by self-contained hinges while the other ends have a resilient overlapping security latch. A series of semi-circular grooves, which are perpendicular to the longitudinal axes of each member, are formed along each of the mating faces and spaced to align with each other. Finally, longitudinally oriented slots are cut through each side of both members near the ends.

In use, each individual line is inserted into one of the grooves, and the separator is snapped close. Strips of hook and loop material are then inserted through the aforementioned slots, and the entire assembly is secured to the bedpost. The result is a neat and orderly arrangement of lines that will not become entangled and can be easily identified. If new medication or nutrition is to be added, it is a simple matter to open the separator and insert a new tube. The task of replacing any individual container is also simplified and accelerated since each line can be easily traced. Most importantly, flow to the patient will not be restricted due to entangled and crimped lines. The present invention may be made in various lengths to accommodate any number of lines.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved intravenous line separator system comprising in combination:
   a cover plate having an upper surface, a lower surface, a first end, and a second end, a plurality of U-shaped grooves formed within the cover plate, a hinge pin positioned within the first end of the cover plate, a C-shaped locking element integral with the second end of the cover plate, a first set of oblong openings positioned within the first end of the cover plate adjacent to the hinge pin, a second set of oblong openings positioned within the second end of the cover plate adjacent to the C-shaped locking element;
   a base plate having an upper surface, a lower surface, a first end, and a second end, a plurality of U-shaped grooves, the U-shaped grooves of the base plate corresponding in number and position to the U-shaped grooves of the cover plate, a hinge pin receiving means positioned at the first end of the base plate, the hinge pin of the cover plate adapted to be received within the hinge pin receiving means, the hinge pin and the hinge pin receiving means together serving to pivotally interconnect the base plate and the cover plate, a tongue locking element integral with the second end of the base plate, the C-shaped locking element adapted to receive the tongue locking element and secure the cover plate to the base plate, a first set of oblong openings positioned within the first end of the base plate adjacent to the hinge pin receiving means, a second set of oblong openings positioned within the second end of the base plate adjacent to the tongue locking element, the first and second set of oblong openings of the cover plate adapted to register with the first and second set of oblong openings of the base plate;

a first strap having a first end and a second end, with the ends thereof provided with a pile type fastener, the first strap adapted to be received within the second set of oblong openings of the cover plate and within the second set of oblong openings of the base plate; and a second strap having a first end and a second end, with the ends thereof provided with a pile type fastener, the second strap adapted to be received within the first set of oblong openings of the cover plate and within the first set of oblong openings of the base plate.

2. An intravenous line separator system comprising:

a cover plate having an upper surface, a lower surface, a first end, and a second end, a plurality of U-shaped grooves formed within the cover plate, a hinge pin positioned within the first end of the cover plate, a C-shaped locking element integral with the second end of the cover plate;

a base plate having an upper surface, a lower surface, a first end, a second end, a plurality of U-shaped grooves, the U-shaped grooves of the base plate corresponding in number and position to the U-shaped grooves of the cover plate, a hinge pin receiving means positioned at the first end of the base plate, the hinge pin of the cover plate adapted to be received within the hinge pin receiving means, the hinge pin and the hinge pin receiving means together serving to pivotally interconnect the base plate and the cover plate, a tongue locking element integral with the second end of the base plate, the C-shaped locking element adapted to receive the tongue locking element and secure the cover plate to the base plate; and at least one strap having a first end and a second end, with a portion thereof between the ends securable to one of the plates and with the ends thereof each provided with a pile type fastener for coupling the strap in a closed loop configuration about a recipient object.

* * * * *